US006793933B2

(12) United States Patent
Cheung

(10) Patent No.: US 6,793,933 B2
(45) Date of Patent: Sep. 21, 2004

(54) DIETARY SUPPLEMENTS FOR ENHANCING THE IMMUNE SYSTEM

(75) Inventor: Ling Yuk Cheung, Hong Kong (HK)

(73) Assignee: Ultra Biotech Limited, Douglas (GB)

( * ) Notice: Subject to any disclaimer, the term of this patent is extended or adjusted under 35 U.S.C. 154(b) by 0 days.

(21) Appl. No.: 10/187,141

(22) Filed: Jun. 28, 2002

(65) Prior Publication Data

US 2004/0001860 A1 Jan. 1, 2004

(51) Int. Cl.[7] .................. A61K 47/00; C12N 13/00; C12N 1/14; C12N 1/16; C12N 1/18
(52) U.S. Cl. .................. 424/439; 424/400; 424/464; 424/489; 424/780; 424/800; 435/173.1; 435/173.8; 435/243; 435/254.1; 435/255.1; 435/255.2; 435/255.21
(58) Field of Search .................. 424/400, 439, 424/464, 489, 780, 800; 435/173.1, 173.8, 243, 254.1, 255.1, 255.2, 255.21, FOR 100, FOR 114

(56) References Cited

U.S. PATENT DOCUMENTS

| | | | |
|---|---|---|---|
| 4,081,367 A | 3/1978 | Hulls et al. | 210/610 |
| 4,183,807 A | 1/1980 | Yoshizawa et al. | 210/611 |
| 4,211,645 A | 7/1980 | Zajic et al. | 210/611 |
| 4,559,305 A | 12/1985 | Zajic et al. | 435/243 |
| 4,816,158 A | 3/1989 | Shimura et al. | 210/610 |
| 5,075,008 A | 12/1991 | Chigusa et al. | 210/610 |
| 5,106,594 A | 4/1992 | Held et al. | 422/292 |
| 5,416,010 A | 5/1995 | Langenberg et al. | 435/468 |
| 5,476,787 A | 12/1995 | Yokoyama et al. | 435/262.5 |
| 5,567,314 A | 10/1996 | Chigusa et al. | 210/150 |
| 5,578,486 A | 11/1996 | Zhang | 435/243 |
| 5,707,524 A | 1/1998 | Potter | 210/606 |
| 5,879,928 A | 3/1999 | Dale et al. | 435/264 |
| 6,036,854 A | 3/2000 | Potter | 210/177 |
| 6,391,617 B1 | 5/2002 | Cheung | 435/254 |
| 6,391,618 B1 | 5/2002 | Cheung | 435/255 |
| 6,391,619 B1 | 5/2002 | Cheung | 435/255 |
| 6,436,695 B1 | 8/2002 | Cheung | 435/254 |
| 6,440,713 B1 | 8/2002 | Cheung | 435/173 |
| 2002/0123127 A1 | 9/2002 | Cheung | 435/254 |
| 2002/0123129 A1 | 9/2002 | Cheung | 435/254 |
| 2002/0123130 A1 | 9/2002 | Cheung | 435/262 |

FOREIGN PATENT DOCUMENTS

| | | |
|---|---|---|
| CN | 1110317 A | 10/1995 |
| EP | 0041373 | 12/1981 |
| FR | 2222433 | 10/1974 |
| JP | 60028893 | 2/1985 |
| RU | 415983 A | 11/1974 |
| RU | 1071637 | 2/1984 |
| WO | WO 87/02705 | 5/1987 |
| WO | WO 95/04814 | 2/1995 |
| WO | WO 99/60142 | 11/1999 |
| WO | WO 02/20431 | 3/2002 |
| WO | WO 02/070682 A2 | 9/2002 |

OTHER PUBLICATIONS

Van den Bogaerde J. et al., "Immune sensitization to food, yeast and bacteria in Crohn's disease," *Alimentary Pharmacology & Therapeutics*, 15:1647–1653 (2001).

(List continued on next page.)

*Primary Examiner*—Thurman K. Page
*Assistant Examiner*—Charesse Evans
(74) *Attorney, Agent, or Firm*—Fish & Neave; James F. Haley, Jr.; Z. Ying Li

(57) ABSTRACT

Compositions comprising a plurality of yeast cells, wherein said plurality of yeast cells are characterized by their ability to enhance the immune system (e.g., increase the activity of T and B lymphocytes and natural killer cells) in a mammal, said ability resulting from their having been cultured in the presence of an alternating electric field having a specific frequency and a specific field strength. Also included are methods of making and using these compositions.

9 Claims, 2 Drawing Sheets

OTHER PUBLICATIONS

Surawicz Christina M. et al., "The search for a better treatment for recurrent Clostridium difficile disease: Use of high–dose vancomycin combined with *Saccharomyces boulardii,*" *Clinical Infectious Diseases*, 31:1012–1017 (2000).

Agarwal N. et al., "Selection of *Saccharomyces cerevisiae* strains for use as a microbial feed additive," *Letters in Applied Microbiology*, 31:270–273 (2000).

Grundler W. et al., "Resonant–like dependence at yeast growth rate on microwave frequencies," *The British Journal of Cancer*, Supplement, England Mar. 1982, 45:206–208 (1982).

Greenwalt C.J. et al., "Kombucha, the fermented tea: Microbiology, composition, and claimed health effects," *Journal of Food Protection*, 63:976–981 (2000).

Mayser P. et al., "The yeast spectrum of the 'tea fungus Kokbucha'," *Mycoses*, Blackwell, Berlin, Germany, 38:289–295 (1995).

Durfresne C. et al., "Tea, Kombucha, and Health: A review," *Food Research International*, 33:409–421 (2000).

Liu C.H. et al., "The Isolation and identification of microbes from a fermented tea beverage, Haipao, and their interactions during Haipao fermentation," *Food Microbiology* (London), 13:407–145 (1996).

Binninger, D. M. et al., "Effects of 60Hz AC magnetic fields on gene expression following exposure over multiple cell generations using *Saccharomyces cerevisiae*", *Bioelectrochemistry and Bioeneretics*, 43(1): 83–89 (1997).

Deguchi, T. et al., "Nylon biodegradation by lignin–degrading fungi", *Applied and Environmental Microbiology*, 63(1): 329–331 (1997).

Pichko, V. B. et al., "Electromagnetic stimulation of productivity of microorganisms and its mechanisms", *Prikladnaya Biokhimiya I Mikrobiologiya*, 32(4): 468–472 (1996).

Ponne, C. T. et al., "Interaction of electromagnetic energy with biological material—relation to food processing", *Radiation Physics and Chemistry*, 45(4): 591–607 (1995).

Van Rensburg, P. et al., "Engineering yeast for efficient cellulose degradation", *Yeast*, 14(1): 67–76 (1998).

"*Saccharomyces cerevisiae* Meyen ex Hansen", China Catalogue of Cultures/China Committee of Culture Collection for Microorganisms (CCCCM), "www.im.ac.cn/database/YEAST/y122.htm", Apr. 24, 1996, retrieved on Nov. 27, 2002.

K. Asami et al., "Real–Time Monitoring of Yeast Cell Divison by Dielectric Spectroscopy", *Biophysical Journal*, 76, pp. 3345–3348 (1999).

E.K. Balcer–Kubiczek et al., "Expression Analysis of Human HL60 Cells Exposed to 60 Hz Square–or Sine–Wave Magnetic Fields", *Radiation Research*, 153, pp. 670–678 (2000).

C.A.L. Basset et al., "Beneficial Effects of Electromagnetic Fields", *Journal of Cellular Biochemistry*, 51, pp. 387–393 (1993).

P. Conti et al., "Effect of Electromagnetic Fields on Several CD Markers and Transcription and Expression of CD4", *Immunobiology*, 201, pp. 36–48 (1999).

A.M. Gonzalez et al., "Effects of an Electric Field of Sinusoidal Waves on the Amino Acid Biosynthesis by Azotobacter", *Z. Naturforsch*, 35, pp. 258–261 (1980).

E.M. Goodman et al., "Effects of Electromagnetic Fields on Molecules and Cells", *International Review of Cytology*, 158, pp. 279–339 (1995).

T. Grospietsch et al., "Stimulating Effects of Modulated 150 MHz Electromagnetic Fields on the Growth of *Escherichia coli* in a Cavity Resonator", *Bioelectrochemistry and Bioenergetics*, 37, pp. 17–23 (1995).

W. Grundler et al., "Nonthermal Effects of Millimeter Microwaves on Yeast Growth", *Z. Naturforsch*, 33, pp. 15–22 (1978).

W. Grundler et al., "Mechanisms of Electromagnetic Interaction with Cellular Systems", *Naturwissenschaften*, 79, pp. 551–559 (1992).

O.I. Ivaschuk et al., "Exposure of Nerve Growth Factor-Treated PC12 Rat Pheochromocytoma Cells to a Modulated Radiofrequency Field at 836.55 MHz: Effects on c–jun and c–fos Expression", *Bioelectromagnetics*, 18, pp. 223–229 (1997).

F. Jelinek et al., "Microelectronic Sensors for Measurement of Electromagnetic Fields of Living Cells and Experimental Results", *Bioelectrochemistry and Bioenergetics*, 48, pp. 261–266 (1999).

A. Lacy–Hulbert et al., "Biological Responses to Electromagnetic Fields", *FASEB Journal*, 12, pp. 395–420 (1998).

C.R. Libertin et al., "Effects of Gamma Rays, Ultraviolet Radiation, Sunlight, Microwaves and Electromagnetic Fields on Gene Expression Mediated by Human Immunodeficiency Virus Promoter", Radiation Research, 140, pp. 91–96 (1994).

H. Lin et al., "Specific Region of the c–myc Promoter Is Responsive to Electric and Magnetic Fields", *Journal of Cellular Biochemistry*, 54, pp. 281–288 (1994).

H. Lin et al., "Magnetic Field Activation of Protein–DNA Binding", *Journal of Cellular Biochemistry*, 70, pp. 297–303 (1998).

L.I. Loberg et al., "Expression of Cancer–Related Genes in Human Cells Exposed to 60 Hz Magnetic Fields", *Radiation Research*, 153, pp.679–684 (2000).

R.L. Moore, "Biological Effects of Magnetic Fields: Studies with Microorganisms", *Canadian Journal of Microbiology*, 25, pp. 1145–1151 (1979).

C.A. Morehouse et al., "Exposure of Daudi Cells to Low-Frequency Magnetic Fields Does Not Elevate MYC Steady–State mRNA Levels", *Radiation Research*, 153, pp. 663–669 (2000).

V. Norris et al., "Do Bacteria Sing? Sonic Intercellular Communication Between Bacteria May Reflect Electromagnetic Intracellular Communication Involving Coherent Collective Vibrational Modes that Could Integrate Enzyme Activities and Gene Expression", *Molecular Microbiology*, 24, pp. 879–880 (1997).

G. Novelli et al., "Study of the Effects on DNA of Electromagnetic Fields Using Clamped Homogeneous Electric Field Gel Electrophoresis", *Biomedicine & Pharmacotherapy*, 45, pp. 451–454 (1991).

J.L. Phillips, "Effects of Electromagnetic Field Exposure on Gene Transcription", *Journal of Cellular Biochemistry*, 51, pp. 381–386 (1993).

V. Romano–Spica et al., "Ets1 Oncogene Induction by ELF–Modulated 50 MHz Radiofrequency Electromagnetic Field", *Bioelectromagnetics*, 21, pp. 8–18 (2000).

J.E. Trosko, "Human Health Consequences of Environmentally–Modulated Gene Expression: Potential Roles of ELF–EMF Induced Epigenetic Versus Mutagenic Mechanisms of Disease", *Bioelectromagnetics*, 21, pp. 402–406 (2000).

C. Ventura et al., "Elf–pulsed Magnetic Fields Modulate Opioid Peptide Gene Expression in Myocardial Cells", *Cardiovascular Research*, 45, pp. 1054–1064 (2000).

A.M. Woodward et al., "Genetic Programming as an Analytical Tool for Non–linear Dielectric Spectroscopy", *Bioelectrochemistry and Bioenergetics*, 48, pp. 389–396 (1999).

T. Yonetani et al., "Electromagnetic Properties of Hemoproteins", *The Journal of Biological Chemistry*, 247, pp. 2447–2455 (1972).

L. Zhang et al., "Electrostimulation of the Dehydrogenase System of Yeast by Alternating Currents", *Bioelectrochemistry and Bioenergetics*, 28, pp. 341–353 (1992).

DIETARY SUPPLEMENTS FOR ENHANCING THE IMMUNE SYSTEM

FIELD OF THE INVENTION

The invention relates to compositions that can alleviate adverse immunological conditions in a mammal and are useful as dietary supplements (e.g., health drinks). These compositions contain yeast cells obtainable by growth in electromagnetic fields with specific frequencies and field strengths.

SUMMARY OF THE INVENTION

This invention is based on the discovery that certain yeast cells can be activated by electromagnetic fields having specific frequencies and field strengths to produce substances that are beneficial for the immune system. Compositions comprising these activated yeast cells can be used as dietary supplements (e.g., health drinks) for improving immunity in a subject in need thereof, e.g., human patients having cancer, viral infection or bacterial infection.

This invention embraces a composition comprising a plurality of yeast cells that have been cultured in an alternating electric field having a frequency in the range of about 17650–17850 MHz (e.g., 17690–17815 or 17696–17811 MHz), and a field intensity in the range of about 50 to 500 mV/cm (e.g., 70–470 or 80–460 mV/cm). The yeast cells are cultured in the alternating electric field for a period of time sufficient to substantially increase the capability of said plurality of yeast cells to produce substances beneficial for the immune system. For instance, the cultured yeast cells when ingested can increase (e.g., by at least 10% such as 20% and 200%) the number of T lymphocytes, the ability of B lymphocytes to proliferate in response to a mitogen (e.g., a lectin such as LPS), and/or the cytotoxicity of natural killer cells in a mammal.

In one embodiment, the frequency and/or the field strength of the alternating electric field can be altered within the aforementioned ranges during said period of time. In other words, the yeast cells can be exposed to a series of electromagnetic fields. An exemplary period of time is about 30–130 hours (e.g., 50 to 105 hours).

Yeast cells that can be included in this composition can all be obtained from the China General Microbiological Culture Collection Center ("CGMCC"), a depository recognized under the Budapest Treaty (China Committee for Culture Collection of Microorganisms, Institute of Microbiology, Chinese Academy of Sciences, Haidian, P.O. BOX 2714, Beijing, 100080, China). Useful yeast species include, but are not limited to, *Saccharomyces cerevisiae* and *Saccharomyces carlsbergensis, Schizosaccharomyces pombe, Saccharomyces sake, Saccharomyces urarum, Saccharomyces rouxii, Hansenula subpelliculosa*, and *Rhodotorula aurantiaca*. For instance, the yeast cells can be of the strain *Saccharomyces cerevisiae* Hansen AS2.375, IFFI1048, AS2.501, AS2.502, AS2.503, AS2.504, AS2.535, AS2.558, AS2.560, AS2.561, or AS2.562; or *Saccharomyces carlsbergensis* AS2.440, or AS2.420.

Also encompassed in the invention are methods of using these compositions to enhance the immune system in an individual and methods of making these compositions.

Unless otherwise defined, all technical and scientific terms used herein have the same meaning as commonly understood by one of ordinary skill in the art to which this invention belongs. Exemplary methods and materials are described below, although methods and materials similar or equivalent to those described herein can also be used in the practice or testing of the present invention. All publications and other references mentioned herein are incorporated by reference in their entirety. In case of conflict, the present specification, including definitions, will control. The materials, methods, and examples are illustrative only and not intended to be limiting. Throughout this specification and claims, the word "comprise," or variations such as "comprises" or "comprising" will be understood to imply the inclusion of a stated integer or group of integers but not the exclusion of any other integer or group of integers.

Other features and advantages of the invention will be apparent from the following detailed description, and from the claims.

DETAILED DESCRIPTION OF THE INVENTION

Figure 1:
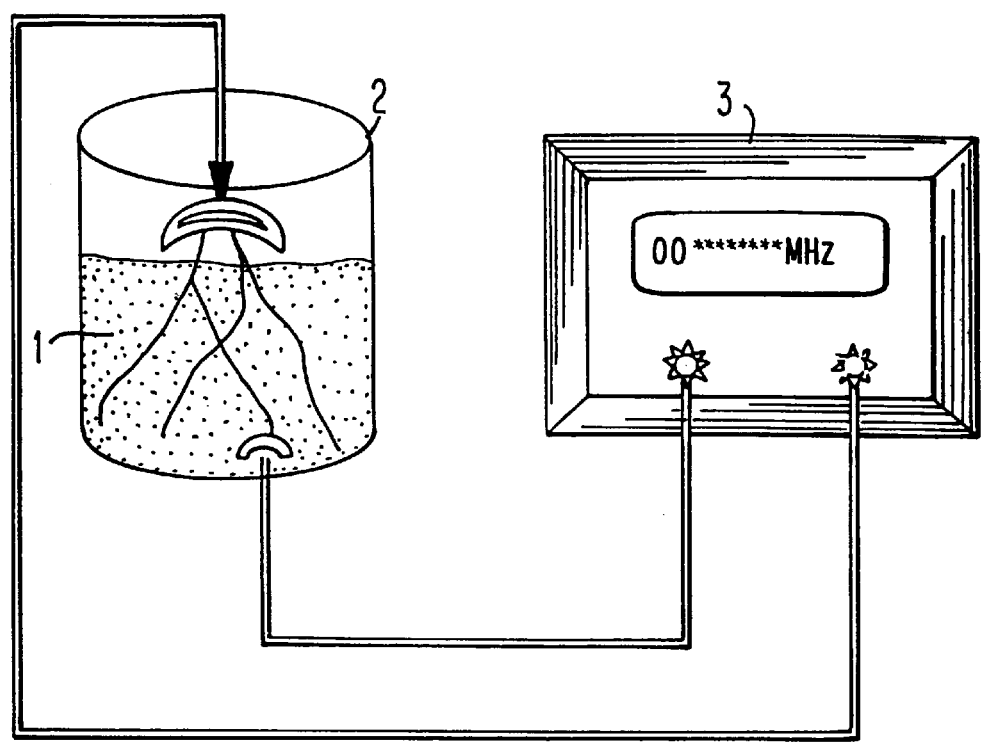
FIG. 1 is a schematic diagram showing an exemplary apparatus for activating yeast cells using electromagnetic fields. 1: yeast culture; 2: container; 3: power supply.

This invention is based on the discovery that certain yeast strains can be activated by electromagnetic fields ("EMF") having specific frequencies and field strengths to produce agents useful in improving immunity. Yeast compositions containing the activated yeast cells can be used as dietary supplements, in the form of health drinks or dietary pills. In certain embodiments, the yeast compositions of this invention can improve immune functions, as indicated by restored activity levels of T cells, B cells and NK cells in immune-compromised subjects (e.g., a human subject).

Since the activated yeast cells contained in these yeast compositions have been cultured to endure acidic conditions (pH 2.5–4.2), the compositions are stable in the stomach and can pass on to the intestines. Once in the intestines, the yeast cells are ruptured by various digestive enzymes, and the anti-aging agents are released and readily absorbed.

Without being bound by any theory or mechanism, the inventor believes that EMFs activate or enhance the expression of a gene or a set of genes in the yeast cells such that the yeast cells become active or more efficient in performing certain metabolic activities which lead to the production of agents that are beneficial for the immune system.

I. Yeast Strains Useful in the Invention

The types of yeasts useful in this invention include, but are not limited to, yeasts of the genera Saccharomyces, Schizosaccharomyces, and Rhodotorula.

Exemplary species within the above-listed genera include, but are not limited to, the species illustrated in Table 1. Yeast strains useful in this invention can be obtained from laboratory cultures, or from publically accessible culture depositories, such as CGMCC and the American Type Culture Collection, 10801 University Boulevard, Manassas, Va. 20110-2209. Non-limiting examples of useful strains (with the accession numbers of CGMCC) are *Saccharomyces cerevisiae* Hansen AS2.501, AS2.502, AS2.503, AS2.504, AS2.535, AS2.558, AS2.560, AS2.561, and AS2.562. In general, yeast strains preferred in this invention are those used for fermentation in the food and wine industries. As a result, compositions containing these yeast cells are safe for human consumption.

Although it is preferred, the preparation of the yeast compositions of this invention is not limited to starting with a pure strain of yeast. A yeast composition of the invention may be produced by culturing a mixture of yeast cells of different species or strains.

TABLE 1

Exemplary Yeast Strains

*Saccharomyces cerevisiae* Hansen

| ACCC2034 | ACCC2035 | ACCC2036 | ACCC2037 | ACCC2038 |
|---|---|---|---|---|
| ACCC2039 | ACCC2040 | ACCC2041 | ACCC2042 | AS2.1 |
| AS2.4 | AS2.11 | AS2.14 | AS2.16 | AS2.56 |
| AS2.69 | AS2.70 | AS2.93 | AS2.98 | AS2.101 |
| AS2.109 | AS2.110 | AS2.112 | AS2.139 | AS2.173 |
| AS2.174 | AS2.182 | AS2.196 | AS2.242 | AS2.336 |
| AS2.346 | AS2.369 | AS2.374 | AS2.375 | AS2.379 |
| AS2.380 | AS2.382 | AS2.390 | AS2.393 | AS2.395 |
| AS2.396 | AS2.397 | AS2.398 | AS2.399 | AS2.400 |
| AS2.406 | AS2.408 | AS2.409 | AS2.413 | AS2.414 |
| AS2.415 | AS2.416 | AS2.422 | AS2.423 | AS2.430 |
| AS2.431 | AS2.432 | AS2.451 | AS2.452 | AS2.453 |
| AS2.458 | AS2.460 | AS2.463 | AS2.467 | AS2.486 |
| AS2.501 | AS2.502 | AS2.503 | AS2.504 | AS2.516 |
| AS2.535 | AS2.536 | AS2.558 | AS2.560 | AS2.561 |
| AS2.562 | AS2.576 | AS2.593 | AS2.594 | AS2.614 |
| AS2.620 | AS2.628 | AS2.631 | AS2.666 | AS2.982 |
| AS2.1190 | AS2.1364 | AS2.1396 | IFFI1001 | IFFI1002 |
| IFFI1005 | IFFI1006 | IFFI1008 | IFFI1009 | IFFI1010 |
| IFFI1012 | IFFI1021 | IFFI1027 | IFFI1037 | IFFI1042 |
| IFFI1043 | IFFI1045 | IFFI1048 | IFFI1049 | IFFI1050 |
| IFFI1052 | IFFI1059 | IFFI1060 | IFFI1062 | IFFI1063 |
| IFFI1202 | IFFI1203 | IFFI1206 | IFFI1209 | IFFI1210 |
| IFFI1211 | IFFI1212 | IFFI1213 | IFFI1214 | IFFI1215 |
| IFFI1220 | IFFI1221 | IFFI1224 | IFFI1247 | IFFI1248 |
| IFFI1251 | IFFI1270 | IFFI1277 | IFFI1287 | IFFI1289 |
| IFFI1290 | IFFI1291 | IFFI1292 | IFFI1293 | IFFI1297 |
| IFFI1300 | IFFI1301 | IFFI1302 | IFFI1307 | IFFI1308 |
| IFFI1309 | IFFI1310 | IFFI1311 | IFFI1331 | IFFI1335 |
| IFFI1336 | IFFI1337 | IFFI1338 | IFFI1339 | IFFI1340 |
| IFFI1345 | IFFI1348 | IFFI1396 | IFFI1397 | IFFI1399 |
| IFFI1411 | IFFI1413 | IFFI1441 | IFFI1443 | |

*Saccharomyces cerevisiae* Hansen Var. *ellipsoideus* (Hansen) Dekker

| ACCC2043 | AS2.2 | AS2.3 | AS2.8 | AS2.53 |
|---|---|---|---|---|
| AS2.163 | AS2.168 | AS2.483 | AS2.541 | AS2.559 |
| AS2.606 | AS2.607 | AS2.611 | AS2.612 | |

*Saccharomyces chevalieri* Guilliermond

AS2.131    AS2.213

*Saccharomyces delbrueckii*

AS2.285

*Saccharomyces delbrueckii* Lindner ver. *mongolicus* (Saito) Lodder et van Rij

AS2.209    AS2.1157

*Saccharomyces exiguous* Hansen

AS2.349    AS2.1158

*Saccharomyces fermentati* (Saito) Lodder et van Rij

AS2.286    AS2.343

*Saccharomyces logos* van laer et Denamur ex Jorgensen

AS2.156    AS2.327    AS2.335

*Saccharomyces mellis* (Fabian et Quinet) Lodder et kreger van Rij

AS2.195

*Saccharomyces mellis* Microellipsoides Osterwalder

AS2.699

*Saccharomyces oviformis* Osteralder

AS2.100

TABLE 1-continued

Exemplary Yeast Strains

*Saccharomyces rosei* (Guilliermond) Lodder et Kreger van Rij

AS2.287

*Saccharomyces rouxii* Boutroux

AS2.178    AS2.180    AS2.370    AS2.371

*Saccharomyces sake* Yabe

ACCC2045

*Candida arborea*

AS2.566

*Candida lambica* (Lindner et Genoud) van. Uden et Buckley

AS2.1182

*Candida krusei* (Castellani) Berkhout

AS2.1045

*Candida lipolytica* (Harrison) Diddens et Lodder

| AS2.1207 | AS2.1216 | AS2.1220 | AS2.1379 | AS2.1398 |
|---|---|---|---|---|
| AS2.1399 | AS2.1400 | | | |

*Candida parapsilosis* (Ashford) Langeron et Talice Var. *intermedia* Van Rij et Verona

AS2.491

*Candida parapsilosis* (Ashford) Langeron et Talice

AS2.590

*Candida pulcherrima* (Lindner) Windisch

AS2.492

*Candida rugousa* (Anderson) Diddens et Lodder

| AS2.511 | AS2.1367 | AS2.1369 | AS2.1372 | AS2.1373 |
|---|---|---|---|---|
| AS2.1377 | AS2.1378 | AS2.1384 | | |

*Candida tropicalis* (Castellani) Berkhout

| ACCC2004 | ACCC2005 | ACCC2006 | AS2.164 | AS2.402 |
|---|---|---|---|---|
| AS2.564 | AS2.565 | AS2.567 | AS2.568 | AS2.617 |
| AS2.637 | AS2.1387 | AS2.1397 | | |

*Candida utilis* Henneberg Lodder et Kreger Van Rij

AS2.120    AS2.281    AS2.1180

*Crebrothecium ashbyii* (Guilliermond)
Routein (*Eremothecium ashbyii* Guilliermond)

AS2.481    AS2.482    AS2.1197

*Geotrichum candidum* Link

| ACCC2016 | AS2.361 | AS2.498 | AS2.616 | AS2.1035 |
|---|---|---|---|---|
| AS2.1062 | AS2.1080 | AS2.1132 | AS2.1175 | AS2.1183 |

*Hansenula anomala* (Hansen) H et P sydow

| ACCC2018 | AS2.294 | AS2.295 | AS2.296 | AS2.297 |
|---|---|---|---|---|
| AS2.298 | AS2.299 | AS2.300 | AS2.302 | AS2.338 |
| AS2.339 | AS2.340 | AS2.341 | AS2.470 | AS2.592 |
| AS2.641 | AS2.642 | AS2.782 | AS2.635 | AS2.794 |

*Hansenula arabitolgens* Fang

AS2.887

*Hansenula jadinii* (A. et R Sartory Weill et Meyer) Wickerham

ACCC2019

*Hansenula saturnus* (Klocker) H et P sydow

ACCC2020

*Hansenula schneggii* (Weber) Dekker

AS2.304

*Hansenula subpelliculosa* Bedford

| AS2.740 | AS2.760 | AS2.761 | AS2.770 | AS2.783 |
|---|---|---|---|---|
| AS2.790 | AS2.798 | AS2.866 | | |

TABLE 1-continued

Exemplary Yeast Strains

*Kloeckera apiculata* (Reess emend. Klocker) Janke

| | | | | |
|---|---|---|---|---|
| ACCC2022 | ACCC2023 | AS2.197 | AS2.496 | AS2.714 |
| ACCC2021 | AS2.711 | | | |

*Lipomycess starkeyi* Lodder et van Rij

| | |
|---|---|
| AS2.1390 | ACCC2024 |

*Pichia farinosa* (Lindner) Hansen

| | | | | |
|---|---|---|---|---|
| ACCC2025 | ACCC2026 | AS2.86 | AS2.87 | AS2.705 |
| AS2.803 | | | | |

*Pichia membranaefaciens* Hansen

| | | | |
|---|---|---|---|
| ACCC2027 | AS2.89 | AS2.661 | AS2.1039 |

*Rhodosporidium toruloides* Banno

ACCC2028

*Rhodotorula glutinis* (Fresenius) Harrison

| | | | | |
|---|---|---|---|---|
| AS2.2029 | AS2.280 | ACCC2030 | AS2.102 | AS2.107 |
| AS2.278 | AS2.499 | AS2.694 | AS2.703 | AS2.704 |
| AS2.1146 | | | | |

*Rhodotorula minuta* (Saito) Harrison

AS2.277

*Rhodotorula rubar* (Demme) Lodder

| | | | | |
|---|---|---|---|---|
| AS2.21 | AS2.22 | AS2.103 | AS2.105 | AS2.108 |
| AS2.140 | AS2.166 | AS2.167 | AS2.272 | AS2.279 |
| AS2.282 | ACCC2031 | | | |

*Rhodotorula aurantiaca* (Saito) Lodder

| | | | | |
|---|---|---|---|---|
| AS2.102 | AS2.107 | AS2.278 | AS2.499 | AS2.694 |
| AS2.703 | AS2.704 | AS2.1146 | | |

*Saccharomyces carlsbergensis* Hansen

| | | | | |
|---|---|---|---|---|
| AS2.113 | ACCC2032 | ACCC2033 | AS2.312 | AS2.116 |
| AS2.118 | AS2.121 | AS2.132 | AS2.162 | AS2.189 |
| AS2.200 | AS2.216 | AS2.265 | AS2.377 | AS2.417 |
| AS2.420 | AS2.440 | AS2.441 | AS2.443 | AS2.444 |
| AS2.459 | AS2.595 | AS2.605 | AS2.638 | AS2.742 |
| AS2.745 | AS2.748 | AS2.1042 | | |

*Saccharomyces uvarum* Beijer

| | | | | |
|---|---|---|---|---|
| IFFI1023 | IFFI1032 | IFFI1036 | IFFI1044 | IFFI1072 |
| IFFI1205 | IFFI1207 | | | |

*Saccharomyces willianus* Saccardo

| | | | | |
|---|---|---|---|---|
| AS2.5 | AS2.7 | AS2.119 | AS2.152 | AS2.293 |
| AS2.381 | AS2.392 | AS2.434 | AS2.614 | AS2.1189 |

*Saccharomyces* sp.

AS2.311

*Saccharomycodes ludwigii* Hansen

| | | |
|---|---|---|
| ACCC2044 | AS2.243 | AS2.508 |

*Saccharomycodes sinenses* Yue

AS2.1395

*Schizosaccharomyces octosporus* Beijerinck

| | |
|---|---|
| ACCC2046 | AS2.1148 |

*Schizosaccharomyces pombe* Lindner

| | | | | |
|---|---|---|---|---|
| ACCC2047 | ACCC2048 | AS2.214 | AS2.248 | AS2.249 |
| AS2.255 | AS2.257 | AS2.259 | AS2.260 | AS2.274 |
| AS2.994 | AS2.1043 | AS2.1149 | AS2.1178 | IFFI1056 |

*Sporobolomyces roseus* Kluyver et van Niel

| | | | | |
|---|---|---|---|---|
| ACCC2049 | ACCC20S0 | AS2.19 | AS2.962 | AS2.1036 |
| ACCC2051 | AS2.261 | AS2.262 | | |

*Torulopsis candida* (Saito) Lodder

| | |
|---|---|
| AS2.270 | ACCC2052 |

*Torulopsis famta* (Harrison) Lodder et van Rij

| | |
|---|---|
| ACCC2053 | AS2.685 |

TABLE 1-continued

Exemplary Yeast Strains

*Torulopsis globosa* (Olson et Hammer) Lodder et van Rij

| | |
|---|---|
| ACCC2054 | AS2.202 |

*Torulopsis inconspicua* Lodder et Kreger van Rij

AS2.75

*Trichosporon behrendii* Lodder et Kreger van Rij

| | |
|---|---|
| ACCC2056 | AS2.1193 |

*Trichosporon capitatum* Diddens et Lodder

| | |
|---|---|
| ACCC2056 | AS2.1385 |

*Trichosporon cutaneum* (de Beurm et al.) Ota

| | | | | |
|---|---|---|---|---|
| ACCC2057 | AS2.25 | AS2.570 | AS2.571 | AS2.1374 |

*Wickerhamia fluorescens* (Soneda) Soneda

| | |
|---|---|
| ACCC2058 | AS2.1388 |

II. Application of Electromagnetic Fields

An electromagnetic field useful in this invention can be generated and applied by various means well known in the art. For instance, the EMF can be generated by applying an alternating electric field or an oscillating magnetic field.

Alternating electric fields can be applied to cell cultures through electrodes in direct contact with the culture medium, or through electromagnetic induction. See, e.g., FIG. 1. Relatively high electric fields in the medium can be generated using a method in which the electrodes are in contact with the medium. Care must be taken to prevent electrolysis at the electrodes from introducing undesired ions into the culture and to prevent contact resistance, bubbles, or other features of electrolysis from dropping the field level below that intended. Electrodes should be matched to their environment, for example, using Ag—AgCl electrodes in solutions rich in chloride ions, and run at as low a voltage as possible. For general review, see Goodman et al., *Effects of EMF on Molecules and Cells*, International Review of Cytology, A Survey of Cell Biology, Vol. 158, Academic Press, 1995.

The EMFs useful in this invention can also be generated by applying an oscillating magnetic field. An oscillating magnetic field can be generated by oscillating electric currents going through Helmholtz coils. Such a magnetic field in turn induces an electric field.

The frequencies of EMFs useful in this invention range from about 17650 MHz to 17850 MHz. Exemplary frequencies include 17696, 17702, 17709, 17806 and 17811 MHz. The field strength of the electric field useful in this invention ranges from about 50 to 500 mV/cm (e.g., 70–90, 160–190, 150–180, 350–380, 440–470, 320–350, 350–400, and 340–380 mV/cm). Exemplary field strengths include 82, 175, 168, 367, 452, 332, 352, 362, 177, 206, and 115 mV/cm.

When a series of EMFs are applied to a yeast culture, the yeast culture can remain in the same container while the same set of EMF generator and emitters is used to change the frequency and/or field strength. The EMFs in the series can each have a different frequency or a different field strength; or a different frequency and a different field strength. Such frequencies and field strengths are referably within the above-described ranges. Although any practical number of EMFs can be used in a series, it may be preferred that the yeast culture be exposed to a total of 2, 3, 4, 5, 6, 7, 8, 9 or 10 EMFs in a series.

Although the yeast cells can be activated after even a few hours of culturing in the presence of an EMF, it may be preferred that the activated yeast cells be allowed to multiply and grow in the presence of the EMF(s) for a total of 30–130 hours, e.g., 30–100, 30–75 or 50–105 hours.

FIG. 1 illustrates an exemplary apparatus for generating alternating electric fields. An electric field of a desired frequency and intensity can be generated by an AC source (3) capable of generating an alternating electric field, preferably in a sinusoidal wave form, in the frequency range of 5 to 20,000 MHz. Signal generators capable of generating signals with a narrower frequency range can also be used. If desired, a signal amplifier can also be used to increase the output. The culture container (2) can be made from a non-conductive material, e.g., glass, plastic or ceramic. The cable connecting the culture container (2) and the signal generator (3) is preferably a high frequency coaxial cable with a transmission frequency of at least 30 GHz.

The alternating electric field can be applied to the culture by a variety of means, including placing the yeast culture (1) in close proximity to the signal emitters such as a metal wire or tube capable of transmitting EMFs. The metal wire or tube can be made of red copper, and be placed inside the container (2), reaching as deep as 3–30 cm. For example, if the fluid in the container (2) has a depth of 15–20 cm, 20–30 cm, 30–50 cm, 50–70 cm, 70–100 cm, 100–150 cm or 150–200 cm, the metal wire can be 3–5 cm, 5–7 cm, 7–10 cm, 10–15 cm, 15–20 cm, 20–30 cm and 25–30 cm from the bottom of the container (2), respectively. The number of metal wires/tubes used can be from 1 to 10 (e.g., 2 to 3). It is recommended, though not mandated, that for a culture having a volume up to 10 L, metal wires/tubes having a diameter of 0.5 to 2 mm be used. For a culture having a volume of 10–100 L, metal wires/tubes having a diameter of 3 to 5 mm can be used. For a culture having a volume of 100–1000 L, metal wires/tubes having a diameter of 6 to 15 mm can be used. For a culture having a volume greater than 1000 L, metal wires/tubes having a diameter of 20–25 mm can be used.

In one embodiment, the electric field is applied by electrodes submerged in the culture (1). In this embodiment, one of the electrodes can be a metal plate placed on the bottom of the container (2), and the other electrode can comprise a plurality of electrode wires evenly distributed in the culture (1) so as to achieve even distribution of the electric field energy. The number of electrode wires used depends on the volume of the culture as well as the diameter of the wires.

III. Culture Media

Culture media useful in this invention contain sources of nutrients that can be assimilated by yeast cells. Complex carbon-containing substances in a suitable form (e.g., carbohydrates such as sucrose, glucose, dextrose, maltose and xylose) can be the carbon sources for yeast cells. The exact quantity of the carbon sources can be adjusted in accordance with the other ingredients of the medium. In general, the amount of carbohydrate varies between about 1% and 10% by weight of the medium and preferably between about 1% and 5%, and most preferably about 2%. These carbon sources can be used individually or in combination. Amino acid-containing substances such as beef extract and peptone can also be added. In general, the amount of amino acid containing substances varies between about 0.1% and 1% by weight of the medium and preferably between about 0.1% and 0.5%. Among the inorganic salts which can be added to a culture medium are the customary salts capable of yielding sodium, potassium, calcium, phosphate, sulfate, carbonate, and like ions. Non-limiting examples of nutrient inorganic salts are $(NH_4)_2HPO_4$, $CaCO_3$, $KH_2PO_4$, $K_2HPO_4$, $MgSO_4$, NaCl, and $CaSO_4$.

IV. Electromagnetic Activation of Yeast Cells

To activate or enhance the ability of yeast cells to produce agents beneficial for the gastrointestinal system, these cells can be cultured in an appropriate medium under sterile conditions at 20–35° C. (e.g., 28–32° C.) for a sufficient amount of time (e.g., 10–150 hours) in an alternating electric field or a series of alternating electric fields as described above.

An exemplary set-up of the culture process is depicted in FIG. 1 (see above). An exemplary culture medium contains the following per 1000 ml of sterile water: 20 g of sucrose, 40 $\mu$g of Vitamin B12 (sterilized and cooled to 45° C. before being added to the solution), 50 $\mu$g of Vitamin C (sterilized and cooled to 45° C. before being added to the solution), 0.2 g of $KH_2PO_4$, 0.2 g of $MgSO_4.7H_2O$, 0.25 g of NaCl, 0.1 g of $CaSO_4.2H_2O$, 3 g of $CaCO_3.5H_2O$, and 2.5 g of peptone. Yeast cells of the desired strain(s) are then added to the culture medium to form a mixture containing $1\times10^8$ cells per 1000 ml of culture medium. The yeast cells can be of any of the strains listed in Table 1. The mixture is then added to the apparatus shown in FIG. 1.

The activation process of the yeast cells involves the following steps: (1) maintaining the temperature of the activation apparatus at 24–33° C. (e.g., 28–32° C.), and culturing the yeast cells for 25–42 hours (e.g., 32 hours); (2) applying an alternating electric field having a frequency of 17696 MHz and a field strength of 160–190 mV/cm (e.g., 175 mV/cm) for 14–18 hours (e.g., 15 hours); (3) then applying an alternating electric field having a frequency of 17702 MHz and a field strength of 150–180 mV/cm (e.g., 168 mV/cm) for 30–35 hours (e.g., 32 hours); (4) then applying an alternating electric field having a frequency of 17709 MHz and a field strength of 350–380 mV/cm (e.g., 367 mV/cm) for 25–30 hours (e.g., 28 hours); (5) then applying an alternating electric field having a frequency of 17806 MHz and a field strength of 440–470 mV/cm (e.g., 452 mV/cm) for 16–20 hours (e.g., 18 hours); and (6) then applying an alternating electric field having a frequency of 17811 MHz and a field strength of 320–350 mV/cm (e.g., 332 mV/cm) for 10–14 hours (e.g., 12 hours). The activated yeast cells are then recovered from the culture medium by various methods known in the art, dried (e.g., by lyophilization) and stored at 4° C. Preferably, the concentration of the dried yeast cells are no less than $10^{10}$ cells/g.

V. Acclimatization of Yeast Cells To the Gastric Environment

Because the yeast compositions of this invention must pass through the stomach before reaching the small intestine, where the effective components are released from these yeast cells, it is preferred that these yeast cells be cultured under acidic conditions to acclimatize the cells to the gastric juice. This acclimatization process results in better viability of the yeasts in the acidic gastric environment.

To achieve this, the yeast powder containing activated yeast cells can be mixed with a highly acidic acclimatizing culture medium at 10 g (containing more than $10^{10}$ activated cells per gram) per 1000 ml. The yeast mixture is then cultured first in the presence of an alternating electric field having a frequency of 17806 MHz and a field strength of 350–400 mV/cm (e.g., 367 mV/cm) at about 28 to 32° C. for 38 to 42 hours (e.g., 40 hours). The resultant yeast cells are further incubated in the presence of an alternating electric field having a frequency of 17811 MHz and a field strength of 340–380 mV/cm (e.g., 352 mV/cm) at about 28 to 32° C. for 20 to 25 hours (e.g., 22 hours). The resulting acclimatized yeast cells are then either dried and stored in powder form ($\geq 10^{10}$ cells/g) at room temperature or in vacuum at 0–4° C.

An exemplary acclimatizing culture medium is made by mixing 700 ml of fresh pig gastric juice and 300 ml of wild Chinese hawthorn extract. The pH of acclimatizing culture medium is adjusted to 2.5 ml of 0.1 M HCl or 0.2 M potassium biphthalate ($C_6H_4(COOK)COOH$). The fresh pig gastric juice is prepared as follows. At about 4 months of age, newborn Holland white pigs are sacrificed, and the entire contents of their stomachs are retrieved and mixed with 2000 ml of water under sterile conditions. The mixture is then allowed to stand for 6 hours at 4° C. under sterile conditions to precipitate food debris. To prepare the wild Chinese hawthorn extract, 500 g of fresh wild Chinese hawthorn is dried under sterile conditions to reduce the water content ($\leq 8\%$). The dried fruit is then ground ($\geq 20$ mesh) and added to 1500 ml of sterile water. The mixture is allowed to stand for 6 hours at 4° C. under sterile conditions. The supernatant is collected to be used in the acclimatizing culture medium.

VI. Manufacture of Yeast Compositions

Figure 2:
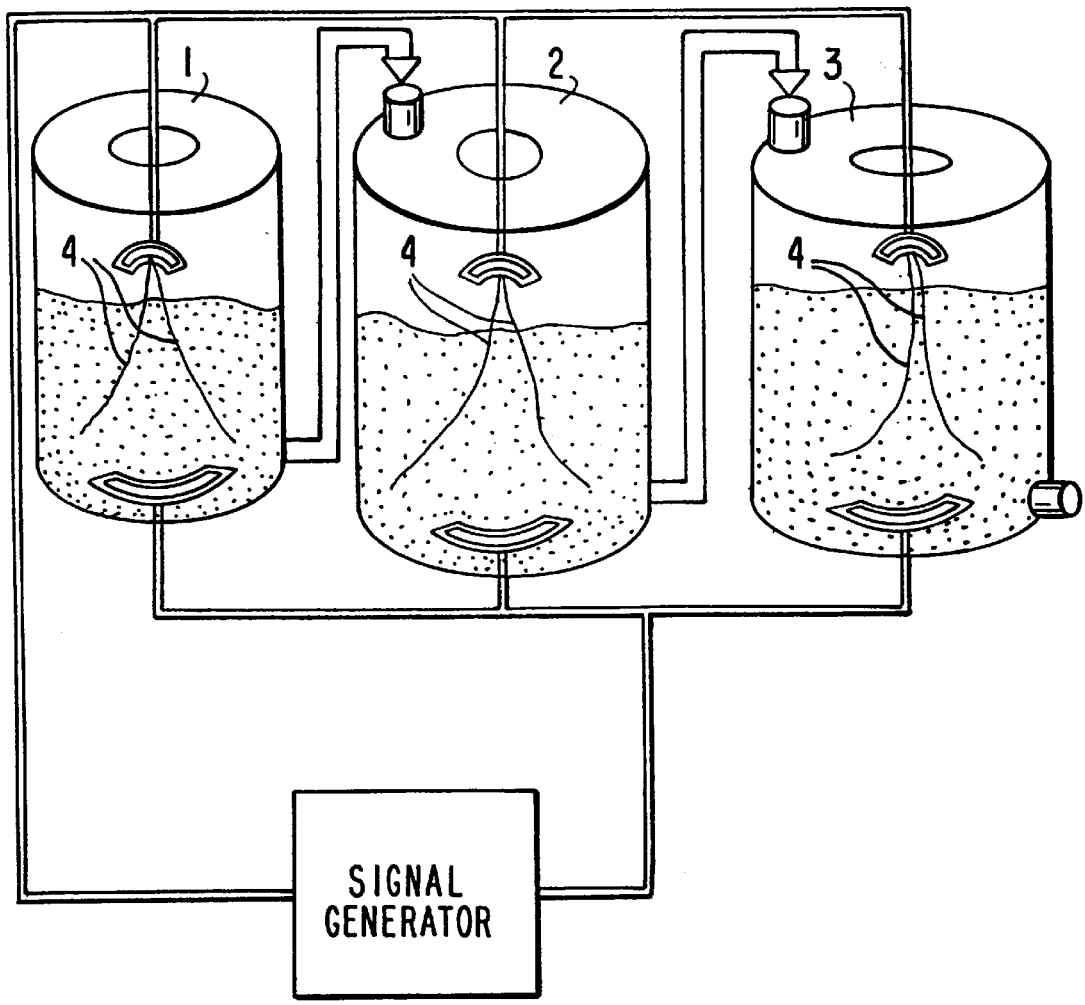
FIG. 2 is a schematic diagram showing an exemplary apparatus for making yeast compositions of the invention. The apparatus comprises a signal generator and interconnected containers 1, 2 and 3.

To manufacture the yeast compositions of the invention, an apparatus depicted in FIG. 2 or an equivalent thereof can be used. This apparatus includes a first container (1), a second container (2), and a third container (3), each equipped with a pair of electrodes (4). One of the electrodes is a metal plate placed on the bottom of the containers, and the other electrode comprises a plurality of electrode wires evenly distributed in the space within the container to achieve even distribution of the electric field energy. All three pairs of electrodes are connected to a common signal generator.

The culture medium used for this purpose is a mixed fruit extract solution containing the following ingredients per 1000 L: 300 L of wild Chinese hawthorn extract, 300 L of jujube extract, 300 L of Wu Wei Zi (*Schisandra chinensis* (Turez) Baill seeds) extract, and 100 L of soy bean extract. To prepare hawthorn, jujube and Wu Wei Zi extracts, the fresh fruits are washed and dried under sterile conditions to reduce the water content to no higher than 8%. One hundred kilograms of the dried fruits are then ground ($\geq 20$ mesh) and added to 400 L of sterile water. The mixtures are stirred under sterile conditions at room temperature for twelve hours, and then centrifuged at 1000 rpm to remove insoluble residues. To make the soy bean extract, fresh soy beans are washed and dried under sterile conditions to reduce the water content to no higher than 8%. Thirty kilograms of dried soy beans are then ground into particles of no smaller than 20 mesh, and added to 130 L of sterile water. The mixture is stirred under sterile conditions at room temperature for twelve hours and centrifuged at 1000 rpm to remove insoluble residues. To make the culture medium, these ingredients are mixed according to the above recipe, and the mixture is autoclaved at 121° C. for 30 minutes and cooled to below 40° C. before use.

One thousand grams of the activated yeast powder prepared as described above (Section V, supra) is added to 1000 L of the mixed fruit extract solution, and the yeast solution is transferred to the first container (1) shown in FIG. 2. The yeast cells are then cultured in the presence of an alternating electric field having a frequency of 17806 MHz and a field strength of about 330–380 mV/cm (e.g., 362 mV/cm) at 28–32° C. under sterile conditions for 14 hours. The yeast cells are further incubated in an alternating electric field having a frequency of 17811 MHz and a field strength of 330–380 mV/cm (e.g., 352 mV/cm). The culturing continues for another 12 hours.

The yeast culture is then transferred from the first container (1) to the second container (2) (if need be, a new batch of yeast culture can be started in the now available the first container (1)), and subjected to an alternating electric field having a frequency of 17806 MHz and a field strength of 130–180 mV/cm (e.g., 177 mV/cm) for 8 hours. Subsequently the frequency and field strength of the electric field are changed to 17811 MHz and 200–210 mV/cm (e.g., 206 mV/cm), respectively. The culturing continues for another ten hours.

The yeast culture is then transferred from the second container (2) to the third container (3), and subjected to an alternating electric field having a frequency of i17806 MHz and a field strength of 90–120 mV/cm (e.g., 115 mV/cm) for 8 hours. Subsequently the frequency and field strength of the electric field are changed to 17811 MHz and 70–90 mV/cm (e.g., 82 mV/cm), respectively. The culturing continues for another 10 hours.

The yeast culture from the third container (3) can then be packaged into vacuum sealed bottles for use as dietary supplements, e.g. tonic drinks. If desired, the final yeast culture can also be dried within 24 hours and stored in powder form. The dietary supplement can be taken three to four 30–60 ml doses daily for a three-month period, preferably 10–30 minutes before meal and bedtime.

In some embodiments, the compositions of the invention can also be administered intravenously or peritoneally in the form of a sterile injectable preparation. Such a sterile preparation can be prepared as follows. A sterilized health drink composition is first treated under ultrasound (1000Hz) for 10 minutes and then centrifuged for another 10 minutes. The resulting supernatant is adjusted to pH 7.2–7.4 using 1 M NaOH and subsequently filtered through a membrane (0.22 µm for intravenous injection and 0.45 µm for peritoneal injection) under sterile conditions. The resulting sterile preparation is submerged in a 35–38 ° C. water bath for 30 minutes before use.

The yeast compositions of the present invention are derived from yeasts used in food and pharmaceutical industries. The yeast compositions are thus devoid of side effects associated with many pharmaceutical compounds.

VII. Examples

The following examples are meant to illustrate the methods and materials of the present invention. Suitable modifications and adaptations of the described conditions and parameters which are obvious to those skilled in the art are within the spirit and scope of the present invention.

The activated yeast compositions used in the following experiments were prepared as described above, using *Saccharomyces cerevisiase* Hansen AS2.503 cells cultured in the presence of an alternating electric field having the electric field frequency and field strength exemplified in the parentheses following the recommended ranges listed in Section IV, supra. Control yeast compositions were those prepared in the same manner except that the yeast cells were cultured in the absence of EMFs.

Example 1

Esterase Staining

Mature T lymphocytes express alpha-naphthyl acetate estarase (ANAE) on their cell surface. The level of ANAE expression is positively correlated to T lymphocyte functions.

In this experiment, 30 NfH mice (6–8 weeks old) were divided into groups A, B and C, each having 10 mice. Mice in these groups were each given 2.5 ml of the activated yeast composition, the control yeast composition and saline, respectively, for 10 consecutive days. On day 10, four hours after the composition administration, 0.5 ml of blood was drawn from the animals from the vena orbitalis, smeared onto a glass slide and blown dry using room temperature air. The slide was then immersed in a 37° C. incubation buffer for 3 hours, rinsed with water to remove debris, and dried carefully with filter paper.

The incubation buffer was prepared as follows. Two grams of α-naphthyl acetate was dissolved in 100 ml of methyl glycol and stored at 4° C. Then 4 g of pararosaniline was dissolved in 100 ml of 2 M HCl. The solution was then warmed up to 60–80° C., filtered, and stored at 4° C. Right before use, 3 ml of freshly made 4% sodium nitrite was added drop-wise to 3 ml of the pararosaniline solution while shaking, until the color changed from brown to light yellow. This solution was a hexazonium pararosaniline solution, usable as an incubation buffer.

The slide was then placed in 89 ml of PB buffer (prepared by mixing 1M $NaH_2PO_4$ and 1M $Na_2HPO_4$ at a 1:1 ratio; pH 7.6), to which 6 ml of the hexazonium pararosaniline solution was slowly added and gently mixed. Then 2.5 ml of the α-naphthyl acetate solution was slowly added while gently mixing the solution. The pH of the solution was subsequently adjusted to 6.4 with acetic acid. Then a 1% malachite green solution was added to the slide and the slide was further incubated for 5–10 seconds. The slide was then rinsed with water, pat dried with filter paper and blown dry with a heat dryer.

The slide was then examined under oil microscope. For each slide, 200 lymphocytes were examined for the presence of red granules in the cytoplasm. A lymphocyte with fine red granules distributed in the cytoplasm was recorded as one (+). A lymphocytes with a single or more larger red granules was recorded as (++). These cells were considered ANAE-positive. A lymphocyte with no red granules was recorded as (−). The percentage of ANAE-positive cells was calculated by dividing the number of (+) cells and (++) cells by 200. The results were shown in Table2 below.

TABLE 2

| Group | Number of Animals | % of esterase-stained T lymphocytes |
|---|---|---|
| A | 10 | 48.89 |
| B | 10 | 34.12 |
| C | 10 | 34.24 |

The data thus demonstrate that the activated yeast composition significantly increased T lymphocyte levels as indicated by ANAE positive cells, as compared to the control yeast composition and saline.

Example 2

Regulation of B Lymphocyte Proliferation

Forty NIH mice (18–22 g) were divided for equal groups A, B, C and D. Mice in group A were orally administered 3 ml of the activated yeast composition per animal daily for 42 consecutive days. Starting on day 14, the mice were placed in an atmosphere with 0.94 ppm ozone for the remaining 28 days. Mice in groups B and C were treated in the same manner except that they were given the control yeast composition and preservative ethyl-p-hydroxy benzoate, respectively. Mice in group D were treated in the same manner as group C except that no ozone treatment was given.

On day 42, the mice were sacrificed by bloodletting from eyeballs. The blood cells were suspended in RPMI-1640 to reach a concentration of $1 \times 10^8$ cells/ml. Then monoclonal antibodies against Thy-1.2 was added to the cell suspension at a ratio of 1:1000. The sample was incubated at 4° C. for 30 seconds and washed once with double distilled water. Then complement was added at a antibody:cell suspension ration of 1:10. The sample was then incubated at 37° C. for 45 minutes, and washed 3 times. The remaining intact cells were counted and suspended in RPMI-1640 at $2.5 \times 10^6$ cells/ml. The cells were then seeded on a 96-well plate, with 0.2 ml in each well. Cells isolated from each mouse were seeded in three duplicate wells. To each well was added 10 μg of lipopolysaccharide (LPS), and the plate was incubated at 37° C. in a humidified atmosphere with 5% $CO_2$ for 72 hours. Sixteen hours before the end of the incubation, $^3$H-TdR was added at 0.5 μCi/well. The radioactivity from each well was measured by standard methods. The data are shown in Table 3 below.

TABLE 3

| Group | Number of Animals | cpm |
|---|---|---|
| A | 10 | 64339 ± 4765 |
| B | 10 | 5221 ± 2141 |
| C | 10 | 5219 ± 1221 |
| D | 10 | 65532 ± 5476 |

These data demonstrate that while ozone markedly inhibited B cell proliferation, the activated yeast composition of this invention significantly reverses that inhibition.

Example 3

Activity of NK Cells

L929 cells are adherent mouse fibroblasts that can uptake neutral red. Thus, the amount of the neutral red uptake after placing NK cells in contact with L929 cells indicates the cytotoxic activity of the NK cells.

In this experiment, 30 NIH mice were divided into three equal groups. Mice in group A were each orally administered 3 ml of the activated yeast composition daily for 14 days. Mice in groups B and C were treated in the same manner, except that they were administered the control yeast composition and preservative ethyl-p-hydroxy benzoate, respectively. On day 14, splenocytes from these animals were prepared using standard techniques. Red blood cells were lysed by suspending the collected splenocytes in 0.4 ml of double-distilled water and gently vortexing the cell sample for 30 seconds. Then 0.4 ml of 1.7% saline was added to restore the osmotic balance of the cell sample. The cells were spun down, washed with serum-free RPMI-1640, and suspended in RPMI-1640 supplemented with 10% fetal bovine serum (FBS) to reach a concentration of $1 \times 10^7$ cells/ml. This preparation contained an enriched population of NK cells.

To prepare target L929 cells, the cells were grown to near confluence one day before the cytotoxicity experiment, and the cell culture medium was replaced with fresh medium. The next day, the cells were trypsinized with 1–2 ml of 0.25% trypsin. The cells were washed off from the culture container with RPMI-1640 and centrifuged at 1000 rpm for 5 minutes. The pellet was resuspended in RPMI-1640 supplemented with 10% FBS at 2×10⁵ cells/ml. The L929 cells were then plated on a flat-bottom 96-well plate at 0.1 ml/well and incubated at 37° C. in a humidified atmosphere with 5% $CO_2$ for at least 1 hour (e.g., 6 hours). Then 0.1 ml of the NK cell solution was added to each well such that the ratio of NK cells to L929 cells was 50:1. Four duplicate wells were used for each sample. RPMI-1640 supplemented with 10% FBS was added to the control wells. The plate was replaced in the 37° C. incubator for at least 20 hours (e.g., 36 hours). The culture medium was then removed, and the wells were washed three times with saline. Then 0.1 ml of 0.1% neutral red was added to each well and incubated at 37° C. for 30 minutes. The dye solution was then removed, and the wells were washed three times with saline. Next, 0.1 ml of a cell lysis solution (50% HCl and 50% ethanol) was added to each well to release neutral red from the L929 cells. Optical density (OD) was measured of each well at 429 nm, with 450 nm as the reference wavelength. Cytotoxic activity of the NK cells was indicated by [(OD of control sample—OD of test sample)/OD of control sample] X 100%, where OD of control sample was the OD of wells with L929 cells only and OD of test sample was the OD of wells with L929 cells and NK cells. The data are shown in Table 4 below.

TABLE 4

| Group | Number of Animals | NK cells O.D. | Cytotoxicity (%) |
|---|---|---|---|
| A | 10 | 0.102 ± 0.021 | 91.2 |
| B | 10 | 0.188 ± 0.042 | 68.3 |
| C | 10 | 0.186 ± 0.022 | 67.9 |

These data demonstrate that the activated yeast composition of the invention can significantly enhance the cytotoxic activity of NK cells.

While a number of embodiments of this invention have been set forth, it is apparent that the basic constructions may be altered to provide other embodiments which utilize the compositions and methods of this invention.

What is claimed is:

1. A composition comprising a plurality of yeast cells, wherein said plurality of yeast cells are characterized by their ability to (1) increase the number of T lymphocytes in a mammal, (2) increase the ability of B lymphocytes to proliferate in response to a mitogen in a mammal, or (3) increase the cytotoxicity of natural killer cells in a mammal, said ability resulting from their having been cultured in the presence of an alternating electric field having a frequency in the range of 17650 to 17850 MHz and a field strength in the range of 50 to 500 mV/cm, as compared to yeast cells not having been so cultured.

2. The composition of claim 1, wherein said frequency is in the range of 17696 to 17811 MHz.

3. The composition of claim 1, wherein said field strength is in the range of 70 to 470 mV/cm.

4. The composition of claim 1, wherein said yeast cells are of the species *Saccharomyces cerevisiae, Saccharomyces carlsbergensis*, or *Hansenula subpelliculosa*.

5. The composition of claim 1, wherein said yeast cells are of the strain deposited at the China General Microbiological Culture Collection Center with an accession number selected from the group consisting of AS2.503, AS2.440, AS2.501, AS2.502, AS2.504, AS2.375, AS2.420, and IFFI1048.

6. The composition of claim 1, wherein the composition is in the form of a tablet, powder, or health drink.

7. The composition of claim 1, wherein the composition is in the form of a health drink.

8. A method of enhancing the immune system in a subject, comprising introducing orally the composition of claim 1 to the subject.

9. A method of preparing a yeast composition, comprising culturing a plurality of yeast cells in the presence of an alternating electric field having a frequency in the range of 17650 to 17850 MHz and a field strength in the range of 50 to 500 mV/cm for a period of time sufficient to substantially increase the capability of said plurality of yeast cells to increase the activity of T lymphocytes, B lymphocytes, or natural killer cells in a mammal.

* * * * *